(12) United States Patent
Ullberg et al.

(10) Patent No.: US 7,561,661 B2
(45) Date of Patent: Jul. 14, 2009

(54) IMAGING ARRANGEMENT AND SYSTEM FOR IMAGING

(75) Inventors: Christer Ullberg, Sollentuna (SE); Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 47 days.

(21) Appl. No.: 11/657,014

(22) Filed: Jan. 24, 2007

(65) Prior Publication Data
US 2008/0101530 A1    May 1, 2008

(30) Foreign Application Priority Data
Oct. 31, 2006   (SE)   .................... 0602292

(51) Int. Cl.
*A61B 6/00*   (2006.01)
(52) U.S. Cl. .......................... 378/19; 378/37
(58) Field of Classification Search ............ 378/37, 378/4–20, 98.8
See application file for complete search history.

(56) References Cited

U.S. PATENT DOCUMENTS

| | | | |
|---|---|---|---|
| 4,349,740 A | 9/1982 | Grassmann et al. | |
| 6,102,866 A | 8/2000 | Nields et al. | |
| 6,337,482 B1 | 1/2002 | Francke | |
| 6,476,397 B1 | 11/2002 | Francke | |
| 6,477,223 B1 | 11/2002 | Francke | |
| 6,522,722 B1 | 2/2003 | Francke | |
| 6,627,897 B1 | 9/2003 | Francke | |
| 6,683,934 B1 * | 1/2004 | Zhao et al. ............ 378/9 |
| 6,784,436 B2 | 8/2004 | Francke | |
| 6,786,868 B2 | 9/2004 | Stotzka et al. | |
| 6,794,656 B2 | 9/2004 | Francke | |
| 6,818,901 B2 | 11/2004 | Francke | |
| 6,856,669 B2 | 2/2005 | Francke | |

(Continued)

FOREIGN PATENT DOCUMENTS

GB    1 562 768    3/1980

(Continued)

OTHER PUBLICATIONS

International Search Report dated Feb. 8, 2008 for corresponding International Application No. PCT/SE2007/000912.

(Continued)

*Primary Examiner*—Courtney Thomas
(74) *Attorney, Agent, or Firm*—Harness, Dickey & Pierce, P.L.C.

(57) ABSTRACT

The invention relates to an imaging arrangement for imaging an object. The imaging arrangement comprises: an X-ray source 5; an X-ray detector 6 arranged to receive X-rays transmitted through the object from the X-ray source 5, wherein the X-ray detector 6 comprises a gaseous-based edge-on direction sensitive line detector provided with an electron avalanche amplifier, and wherein the line detector is adapted to record a line image of radiation as transmitted through the object; and a support device 8 to which the X-ray source 5 and the X-ray detector 6 are attached so as to be arranged on opposite sides of the object, and wherein the support device 8 is arranged to rotate around the object and is also arranged to be movable in relation to the object. The invention also relates to a system comprising such imaging arrangement.

18 Claims, 4 Drawing Sheets

U.S. PATENT DOCUMENTS

| | | | |
|---|---|---|---|
| 6,873,682 | B2 | 3/2005 | Francke |
| 6,940,942 | B2 | 9/2005 | Ullberg |
| 6,970,533 | B2 | 11/2005 | Francke |
| 7,006,597 | B2 | 2/2006 | Francke |
| 7,016,458 | B2 | 3/2006 | Francke |
| 2003/0174806 | A1* | 9/2003 | Francke et al. ............... 378/37 |
| 2004/0081273 | A1* | 4/2004 | Ning ........................... 378/37 |
| 2005/0117694 | A1 | 6/2005 | Francke |
| 2005/0288581 | A1* | 12/2005 | Kapur et al. ................ 600/437 |
| 2006/0262898 | A1* | 11/2006 | Partain et al. ............... 378/37 |

FOREIGN PATENT DOCUMENTS

| | | |
|---|---|---|
| WO | WO 01/67134 | 9/2001 |
| WO | WO 02/101414 | 12/2002 |
| WO | WO 2004/091405 | 10/2004 |
| WO | WO 2006/098689 | 9/2006 |

OTHER PUBLICATIONS

P. Despres, et al.—Physical characteristics of a low-dose gas microstrip detector for orthopedic x-ray imaging—Med. Phys. 32 (4), Apr. 2005, AN 8366924.

International Search Report dated May 9, 2007 issued in National Application No. 0602292-5, filed Oct. 31, 2006.

* cited by examiner

IMAGING ARRANGEMENT AND SYSTEM FOR IMAGING

PRIORITY STATEMENT

This application claims benefit of priority under 35 U.S.C. § 119 from Swedish Patent Application No. 0602292-5 filed on Oct. 31, 2006, in the Swedish Patent Office, the disclosure of which is incorporated herein by reference in its entirety.

FIELD OF THE INVENTION

The present invention relates to the field of cone beam computed tomography scanning, and in particular to an imaging arrangement and a system for imaging by means of such cone beam computed tomography.

BACKGROUND OF THE INVENTION

Computed Tomography Scanning (CT scanning), also denoted computerized tomography or computed axial tomography (CAT), is a medical imaging method employing imaging by sectioning or 3D reconstruction. In the CT-scanning an X-ray source and an X-ray detector are arranged opposite one another on an arrangement that rotates around a patient. The X-ray source transmits radiation through the patient and the X-ray detector measures the attenuated radiation. The radiation is converted to an electrical signal, a computer processes these signals and the desired images can be provided.

An important improvement of the two-dimensional scanning was made with the introduction of the so-called spiral or helical scan. Instead of scanning the patient on a two-dimensional basis, the patient is scanned on a three-dimensional basis. In particular, the table on which the patient rests moves through the scanning field at a constant speed while the X-ray tube and X-ray detector rotates around the patient.

Digital geometry processing is used to generate a three-dimensional image of the internals of an object from a large series of two-dimensional X-ray images taken around a single axis of rotation.

The X-ray arrangement is rotated one revolution, then moved a small step and rotated again. Alternatively, in the spiral scan the X-ray arrangement moves in a helical movement with a small pitch for each revolution. The speed of rotation is normally a few revolutions per second.

SUMMARY OF THE INVENTION

CT systems of today use rather narrow detectors with a small field of view in the translation direction. The detector is typically only 0.5-30 mm wide. There is a desire in CT imaging to make the detector wider in order to reduce the number of revolutions needed to image the organ or object of interest. The existing CT detectors use light sensitive CMOS detectors with scintillators emitting light when struck by X-rays. This detector technology cannot be used for implementing wide detectors due to the high costs and problems to read out the signals from a wider detector. An alternative being investigated is the use of area detectors, so called cone beam CT. These area detectors are made of for example thin film transistor (TFT) panels. Such TFT-panels are currently used for 2D X-ray imaging.

However, the TFT-panels have a number of limitations when it comes to cone beam CT imaging. Firstly, they are slow to read out and can at most be read out 60 times per second, but then with rather large pixel size. Small pixel sizes can typically only be read out 5-10 times per second. This is far too slow for CT applications when one wishes to read out the detector one thousand times per revolution or more. Secondly, the TFT-panels have too high electronic noise, which adds up when thousands of images are combined to form the CT slice images or 3D volumes. Thirdly, area detectors are sensitive to X-rays that scatter in the patient and hit the detector in an arbitrary position, causing a foggy appearance in the X-ray images. These scattered X-rays are normally suppressed by arranging a grid between the patient and the detector. The grid is moved much faster than the detector readout frequency in order to prevent a shadow image to be formed from the grid. When it comes to area detectors that need to be read out thousands of times each second it is both difficult to construct a grid that shields well enough and that can be moved much faster than the readout frequency without causing artefacts in the images. Fourthly, the TFT detectors have residual ghost images present that add noise to the succeeding images. They also often saturate for high X-ray fluxes causing the signal to bloom out over several pixels.

It would be desirable to provide cone beam CT-scanning in which a larger number of images could be taken without degrading the image quality, more specifically somewhere between 100 and 5000 images in each rotation of the X-ray arrangement, when rotating 0.5-5 revolutions per second. This would set high demands on the detector, for example in terms of readout speed. The detector would have to be able to rapidly detect radiation transmitted from the X-ray source, and to quickly transfer the data from the detector to a buffer memory or to a computer from each readout. Further, in order to obtain usable images, that is, images having a high enough resolution, the size of the pixels have to be small, preferably within the range of 0.05-0.1 mm. The detectors used in cone beam CT-scanning today cannot meet these demands; they are simply not fast enough to take such high-resolution images at the required speed.

Further yet, the detector used in a cone beam CT-scanning has to be able to shield radiation scattered from the object being imaged. As mentioned, scattered radiation appears as noise and is added in the reconstructed image. It is difficult to prevent this kind of noise; it is for example difficult to efficiently shield the detector by means of a grid or the like.

In medical applications of X-ray imaging it is important to minimize the radiation dose that the patient is subjected to. It is also important that the examination procedure is as comfortable as possible and that the procedure is carried out as fast as possible.

Further, it is important that the X-ray imaging system can be manufactured at a reasonable cost.

In view of the above it would be desirable to provide an in many aspects improved arrangement and system for imaging objects, and in particular medical imaging by means of cone beam computed tomography.

It is an object of the invention to provide an imaging arrangement and system for imaging an object that overcomes or at least alleviates the shortcomings of the prior art. In particular, an object is to provide a system for imaging an object wherein an increased quality of images taken can be provided, while still enabling the imaging procedure to be performed quickly.

It is another object of the invention to provide such a system, the construction of which is less complicated. In particular, it is an object to provide a system wherein the need for shielding devices can be eliminated.

It is yet another object to increase the quality in terms of resolution and noise levels of the images taken, thereby increasing the quality of a conclusion drawn or a diagnosis made based on the images.

Still another object of the invention is to lessen the discomfort of the patient undergoing an examination in the form of imaging a body part, such as a breast.

These objects, among others, are achieved by a system for imaging and by a method for imaging as claimed in the independent claims.

In accordance with the invention, an imaging arrangement for imaging an object is provided. The imaging arrangement comprises: an X-ray source; an X-ray detector arranged to receive X-rays transmitted through the object from the X-ray source, wherein the X-ray detector comprises a gaseous-based edge-on direction sensitive line detector provided with an electron avalanche amplifier, and wherein the line detector is adapted to record a line image of radiation as transmitted through the object; and a support device to which the X-ray source and the X-ray detector are attached so as to be arranged on opposite sides of the object, and wherein the support device is arranged to rotate around the object. The support device is also arranged to be linearly movable in relation to the object. That is, the support device is movable vertically or horizontally with respect to the object. Alternatively, the object is translated in a vertical or horizontal direction while the support device is rotated around the object. By means of the imaging arrangement, a computerized tomography image can be provided.

The imaging arrangement in accordance with the present invention can be read out up to 25 000 times per second or even faster. The resolution is high and the pixel size is small, down to 0.05 mm. The photon counting and gaseous avalanche amplification ensures that there is no noise contributing to the image, besides the statistical fluctuation of the X-ray photon flux. The detector has no lag, ghosting or blooming effects. Further, the performance of the imaging arrangement is not degraded by scattered radiation. The gaseous-based line detector discriminates more than 99% of the scattered photons. Further yet, the imaging arrangement can be made very cost-efficient and the X-ray detector of the imaging arrangement provides an excellent X-ray detector for cone beam CT scanning.

The present invention provides an imaging system with a detector that is intrinsically blind to scattered X-rays without the need of a grid. By using a directional sensitive detector the scattering problems in prior art are eliminated.

Further characteristics of the invention and advantages thereof will be evident from the detailed description of a preferred embodiment of the present invention given hereinafter and the accompanying figures, which are only given by way of illustration, and thus are not limitative of the present invention.

DETAILED DESCRIPTION OF EMBODIMENTS

In the following the present invention is described and exemplified by means of a particular medical application, namely mammography. The invention is however applicable in other areas as well, with suitable modifications.

Mammography is an example of an important application of medical imaging. In a mammography procedure of today the breast of the patient is compressed between two compression plates and the X-ray source is activated and the X-ray detector captures a 2D image of the breast. The compression of the breast is most uncomfortable to the patient. Further, it is important that the image quality is high, since breast cancer can, for example, be missed by being obscured by radiographically dense, fibrograndular breast tissue. There are thus a number of drawbacks related to the field of mammography. These drawbacks, among others, are overcome by means of the present invention.

Figure 1:
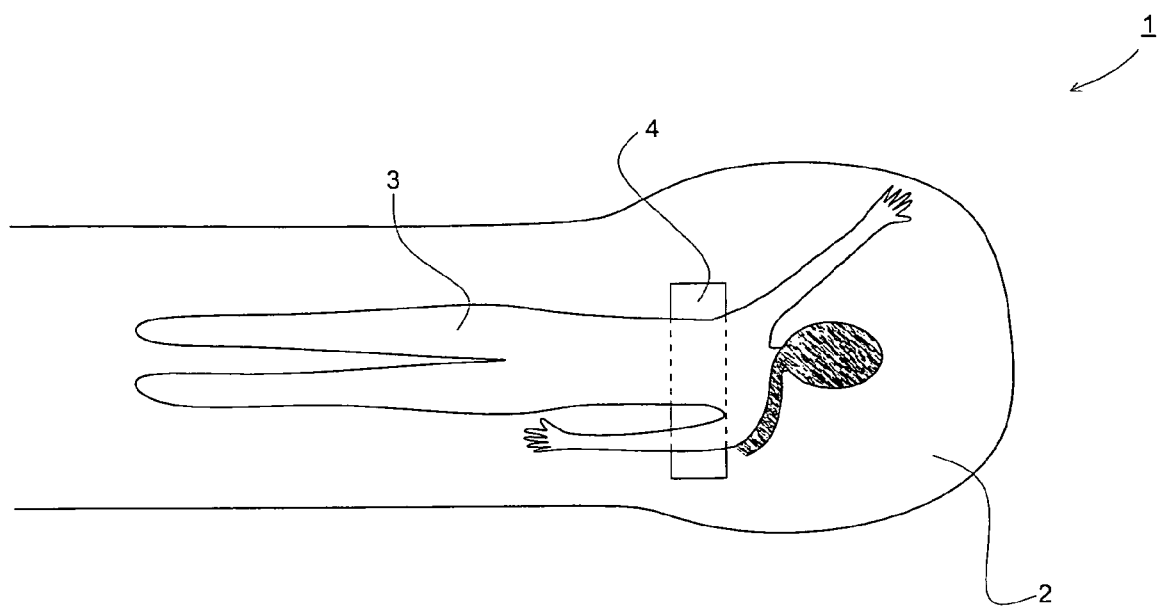
FIG. 1 is a top view of a patient positioning table.

FIG. 1 illustrates schematically the present invention in a mammography application. A system 1 for medical imaging comprises a patient positioning table 2 on which the patient 3 rests face down. The patient thereby rests comfortably on a horizontal examination table during the whole examination. The patient positioning table 2 comprises a suitably located opening 4 in which the patient places her breasts.

Figure 2:
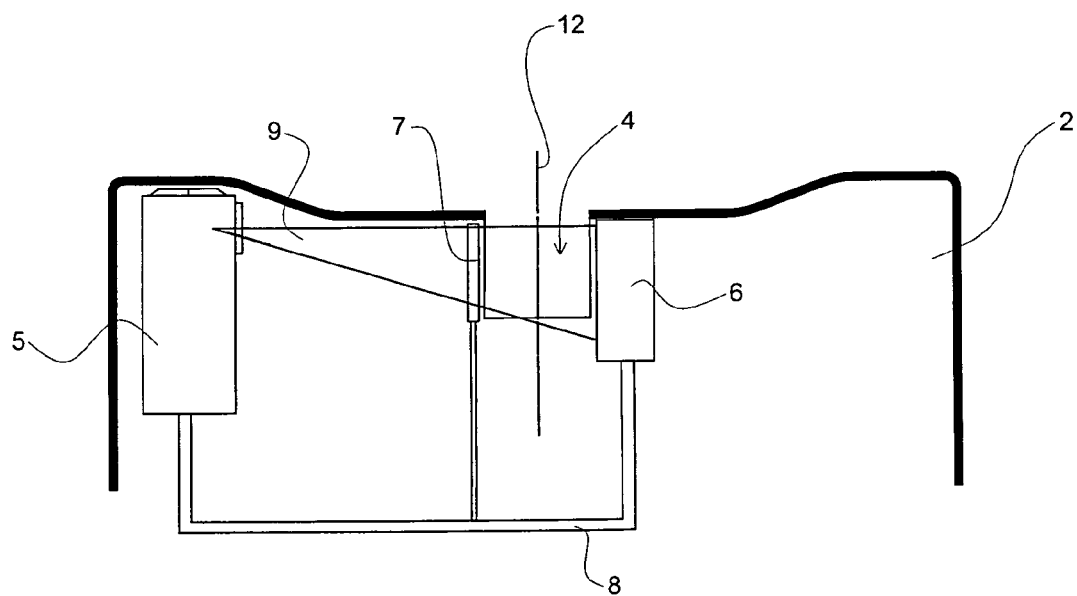
FIG. 2 is a side view of the patient positioning table of FIG. 1, showing an imaging arrangement used in accordance with the invention.

FIG. 2 illustrates the system 1 of FIG. 1 in a cross-sectional view. An imaging arrangement is provided underneath the patient positioning table 2. The imaging arrangement comprises an X-ray source 5, a collimator 7 and an X-ray detector 6 attached to a support device 8, for example a common E-arm. The support device 8 is illustrated very schematically in the figure and it is realized that any suitable support structure may be utilized. The X-ray source 5 and the X-ray detector 6 are arranged on the support device 8 on opposite sides of the object to be imaged, the object being, in the illustrated example, the breast of a patient. The X-ray detector 6 is thereby able to measure the radiation transmitted from the X-ray source 5 and through the breast of the patient 3.

The imaging arrangement, that is, the support device 8 comprising the X-ray source 5, the collimator 7 and the X-ray detector 6 rotate around the object to be imaged. The object, i.e. the breast; hangs down in a vertical direction while being imaged. There is no need to compress the breast but the breast should be held still during the procedure. The rotation axis of the imaging arrangement is vertically through the breast, the axis of rotation being indicated at 12.

While rotating the imaging arrangement 5, 6, 7, 8 it is simultaneously moved in the vertical direction. The vertical movement can be made in a helical movement, i.e. a vertical movement simultaneously with the rotation. Alternatively, the imaging arrangement may be held still while rotating one revolution, then the imaging arrangement is moved a suitable distance in the vertical direction, for example 0.1-1 mm and the imaging arrangement is again rotated one revolution and so on.

Alternatively, instead of moving the imaging arrangement, the object is translated parallel to the rotation axis, i.e. moved up or down, while the support device 8 is only rotated around the object.

Furthermore, the imaging arrangement 5, 6, 7, 8 comprises a microprocessor or computer (not shown) provided with suitable software for controlling the arrangement and readout and post-processing of the data recorded by the X-ray detector 6. In particular, the computer comprises computing means for generating a three-dimensional image of the internals of the object from a large series of two-dimensional X-ray images taken around a single axis of rotation. In short, means are provided for creating three-dimensional computerized tomography images. Further, a power supply (not shown) is included for supplying the X-ray detector 6 and the microprocessor or computer with power.

Figure 3:
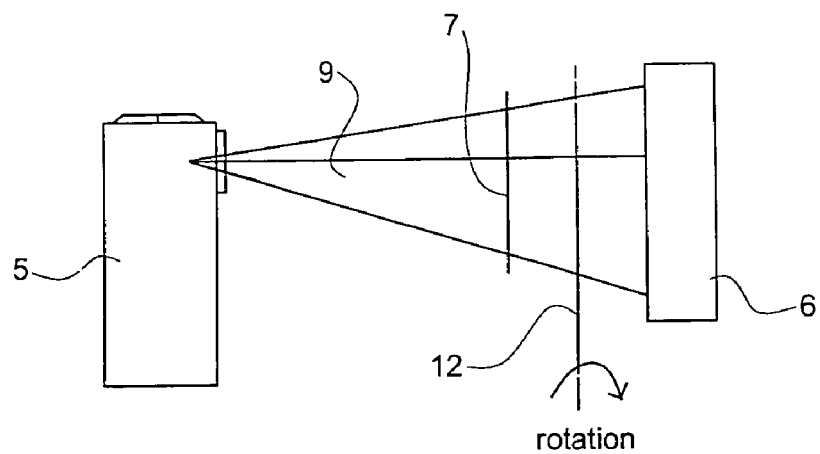
FIG. 3 illustrates X-ray source and X-ray detector of the imaging arrangement used in the present invention.

The X-ray source 5, the collimator 7 and the X-ray detector 6 are next described more in detail with reference to FIG. 3.

The X-ray source 5 preferably comprises one or more X-ray tubes having a cathode, which emits electrons, and an anode, which emits X-rays in response to being struck by the electrons.

The collimator 7 may be a thin foil of e.g. tungsten. The collimator 7 prevents radiation, which is not directed directly towards the X-ray detector 6, from impinging on the object, thereby reducing the radiation dose to the object. This is advantageous in particular in all applications where the object is a human or an animal, or parts thereof.

Figure 4:
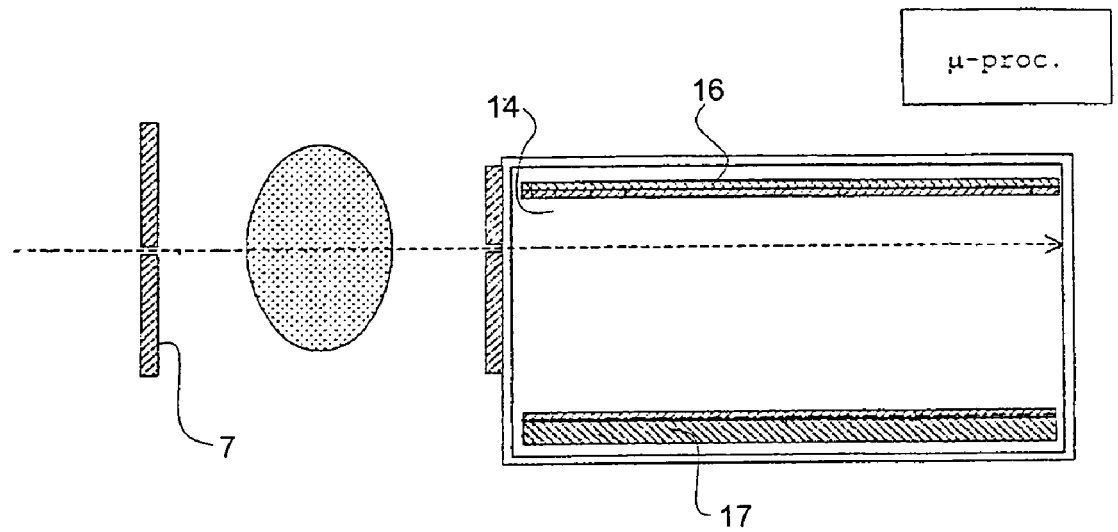
FIG. 4 illustrates a line detector of the X-ray detector shown in FIG. 3.

With reference to FIG. 4, a line detector of the X-ray detector 6 is illustrated. The line detector comprises a chamber 14, preferably a gas or liquid tight chamber, filled with an ionizable substance, which is also suitable for electron avalanche amplification. The substance is preferably a gas such as a noble gas, carbondioxide, ethane, methane, iso-butane or a combination thereof. It can also be a noble gas in liquid or solid form. The gas may be under pressure, preferably in a range 1-20 atm.

The line detector is oriented such that a planar X-ray beam 9 can enter sideways between a first electrode, a cathode arrangement 16, and a second electrode, being an anode arrangement 17. The X-ray detector 6 thus comprises an electrode arrangement including a cathode 16, an anode 17, and acceleration or amplification electrode arranged in between the cathode 16 and the anode 17. The electrodes 16 and 17 are essentially planar and parallel with each other and oriented with respect to the radiation entrance such that the radiation can enter the X-ray detector 6 between and substantially parallel with the cathode and electrode.

During use, the electrodes 16 and 17 are held at electric potentials such that a strong amplification field is created between cathode 16 and anode 17 for gaseous avalanche amplification of the electrons released as a result of ionization of the substance in the chamber 14. Multiple avalanche electrons thus reach one of the electrodes 17, which also may constitute a read-out arrangement of the detector 6 for detection of pulses induced by the electron avalanches. The read-out arrangement is connected to the microprocessor, mentioned earlier, for further processing of the detected pulses.

In accordance with the invention, the X-ray detector 6 comprises a plurality of direction sensitive line detectors arranged in an array, each extending in a horizontal direction in order to record one-dimensional images in the horizontal direction. Each of the line detectors is preferably a gaseous-based ionization detector, as described above, wherein electrons freed as a result of ionization by ionizing radiation entered into the line detector are accelerated, and optionally avalanche amplified, in a direction essentially perpendicular to the direction of the entered ionizing radiation. Such line detector is referred to as a gaseous-based edge-on detector.

Such line detectors and arrays thereof are further described in the following U.S. Pats. issued to Tom Francke at al.: U.S. Pat. Nos. 6,337,482; 6,477,223; 6,476,397; 7,016,458; 7,006,597; 6,940,942; 6,970,533; 6,856,669; 6,873,682; 6,784,436; 6,794,656; 6,818,901; 6,627,897; 6,627,897; and 6,522,722, as well as in references therein, all of which being hereby incorporated by reference.

The above described embodiment, wherein the X-ray detector 6 comprises a stack of line detectors 6a, 6b, ..., 6n is described somewhat more in detail in the following, with reference to FIG. 5. Each line detector 6a, 6b, ..., 6n is directed towards the divergent X-ray source 5 to allow a respective ray bundle $b_1, \ldots, b_n, \ldots, b_N$ of the radiation 9 that propagates in a respective one of a plurality of different angles $\alpha_1, \ldots, \alpha_n, \ldots, \alpha_N$ with respect to the front surface of the X-ray detector 6 to enter the respective line detector.

The collimator 7 may have narrow radiation transparent slits etched away, wherein the number of the slits corresponds to the number of line detectors 6a, 6b, ..., 6n of the X-ray detector 6. The slits are aligned with the line detectors 6a, 6b, ..., 6n so that X-rays passing through the slits of the collimator 7 will reach the line detectors 6a, 6b, ..., 6n, i.e. as the respective ray bundles $b_1, \ldots, b_n, \ldots, b_N$.

Figure 5:
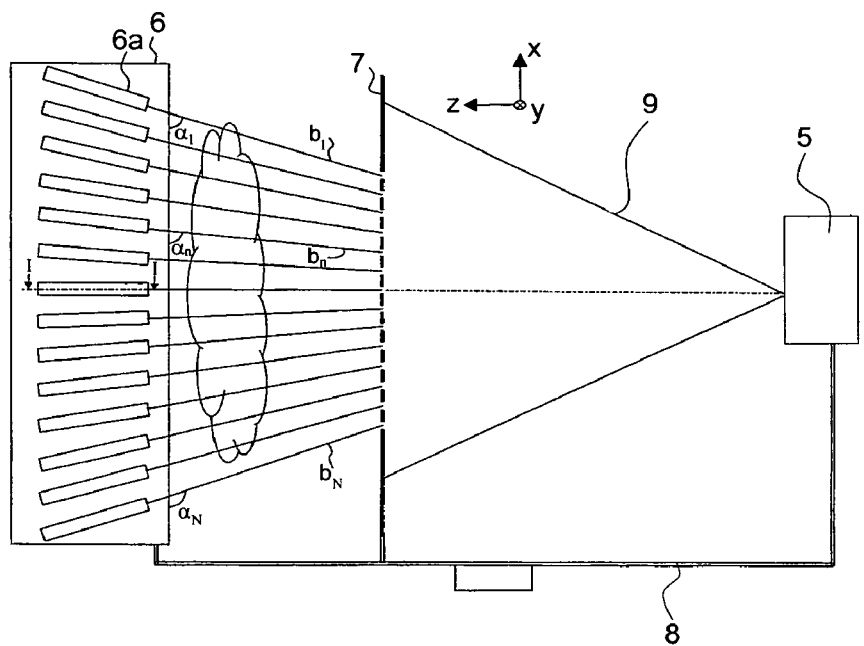
FIG. 5 is another illustration of the X-ray detector utilized in the present invention.

During the rotation of the support device 8 around the x-axis indicated in FIG. 5, preferably around an axis in the x-direction passing through the object to be imaged, the X-ray detector 6, and in particular the line detectors 6a, 6b, ..., 6n of the X-ray detector 6, registers the radiation passed through the object. In one revolution, a two-dimensional image per line detector 6a, 6b, ..., 6n of the internals of the object is provided based on these registrations. That is, during one revolution a corresponding internal layer of the object is imaged by each line detector 6a, 6b, ..., 6n.

During the translational movement in the x-direction in FIG. 5 (i.e. scanning) of the support device 8, the X-ray source 5 and the X-ray detector 6 are moved relative the object in a linear manner, while each of the line detectors 6a, 6b, ..., 6n records a plurality of line images of radiation as transmitted through the object in a respective one of the different angles $\alpha_1, \ldots, \alpha_n, \ldots, \alpha_N$. That is, a number of imaged layers of the internals of the object can now be computed and a computerized tomography image is provided.

The scanning of the object is performed a length, which is sufficiently large so that each one of the line detectors can be scanned at least across the distance between two adjacent line detectors, typically about 1-10 mm.

By using the X-ray detector 6 described above, all of the problems described in the introductory part are eliminated or at least greatly alleviated. More specifically, the X-ray detector 6 enables at least 25 000 read outs per second to be made. The resolution is high, and the pixel size is preferably within the range of 0.05-0.1 mm. The photon counting and gaseous avalanche amplification ensures that no noise will occur. Further, the performance of the X-ray detector 6 is not degraded by scattered radiation. Further yet, the imaging arrangement can be made very cost-efficient and provides an excellent X-ray detector 6 for cone beam CT scanning. The above-described gaseous-based line detector discriminates more than 99% of the scattered photons.

The detector 6 may be any other type of direction sensitive line detector based on for example PIN diodes, CCD or CMOS arrays.

Figure 6:
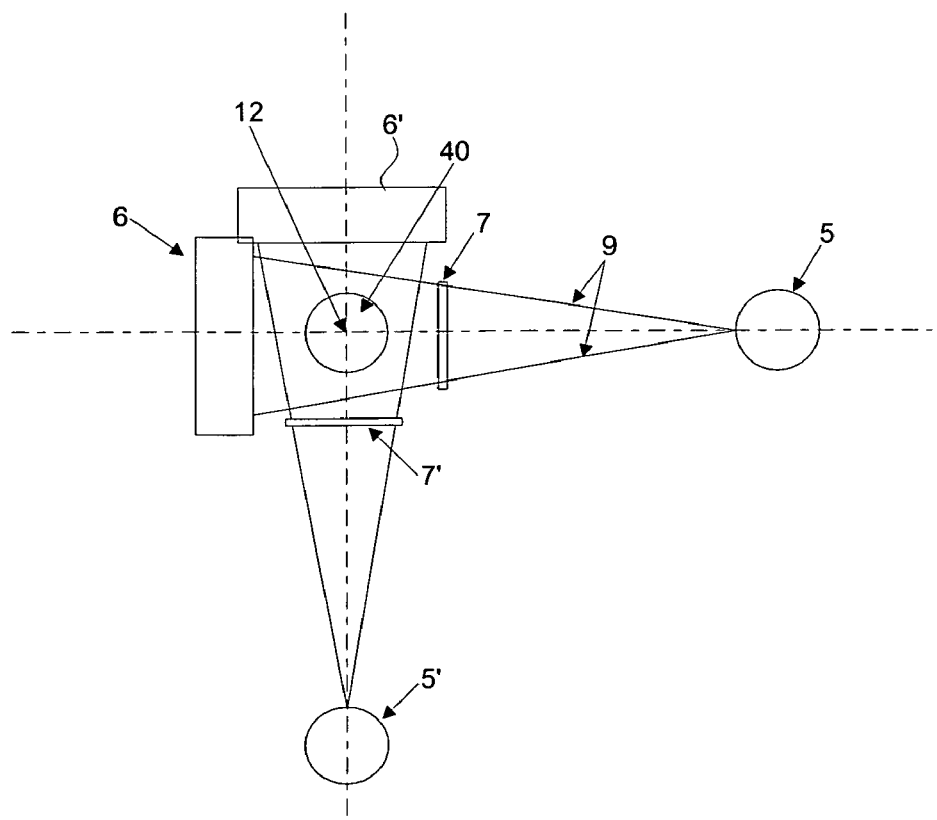
FIG. 6 illustrates another embodiment of the invention.

In another embodiment of the invention, illustrated in FIG. 6, the system 1 comprises two imaging arrangements, that is, two X-ray sources 5, 5', two X-ray detectors 6, 6' and two collimators 7, 7'. Each imaging arrangement comprises one X-ray source, one X-ray detector and one collimator as above. The two imaging arrangements are suitably arranged, for example forming an angle of 90° between the respective parts of the imaging arrangements, as illustrated in the figure. Yet additional imaging arrangements could be arranged around the object 40 to be imaged, in dependence on the size of the imaging arrangements.

Several advantages are achieved by this embodiment. Images can be taken faster owing to the increased amount of X-ray flux. Further, if the two imaging arrangements are displaced along the vertical axis 12 in relation to each other, then the support device 8 holding the imaging arrangements can be moved half the distance between the two X-ray detectors 6, 6' in the vertical direction. Further yet, the X-ray sources 5, 5' may have different energies, so as to provide dual energy imaging. This is particularly advantageous if a contrast agent such as iodide is used.

Such dual energy imaging can also be accomplished by using a single imaging arrangement. A filter device in front of the collimator 7 can be used for providing such dual-energy imaging. A filter device capable of operating in two or more operation modes having different filter characteristics is disclosed in EP1613216, assigned to the same applicant as the present application. A control device may be arranged to alter the operation mode of the filter device.

Figure 7:
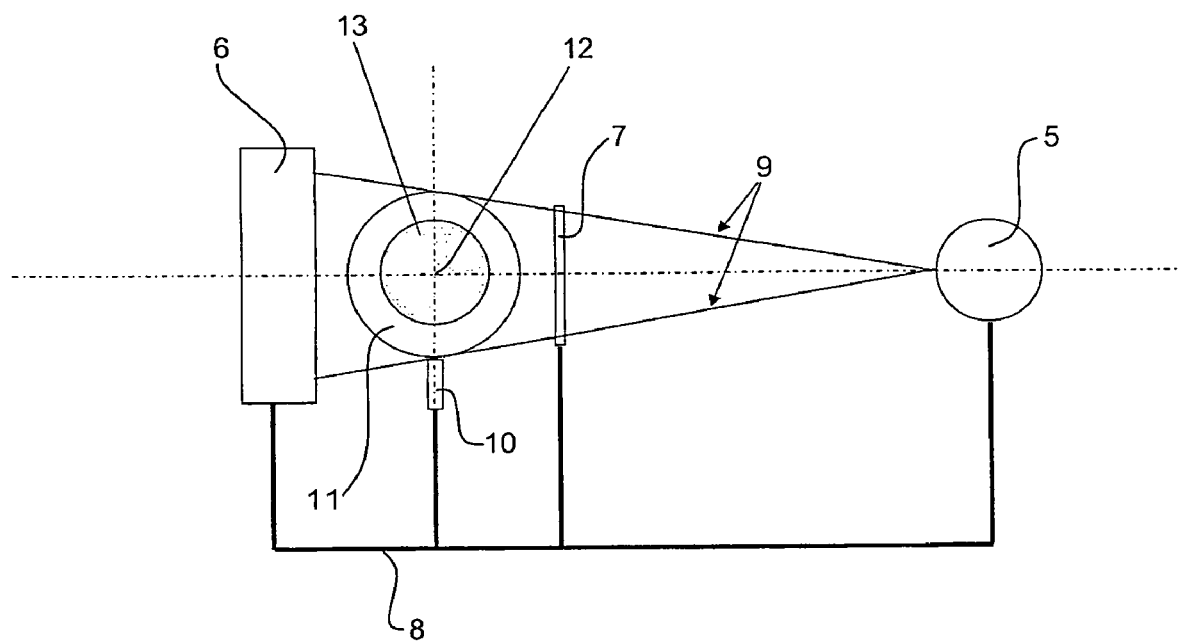
FIG. 7 illustrates still another embodiment of the invention.

In yet another embodiment of the invention, illustrated in FIG. 7, the imaging arrangement further comprises an ultrasonography device 10. Medical ultrasonography, or simply sonography, is an ultrasound-based diagnostic imaging technique and is used for imaging internal organs of a patient. Ultrasonography is prevailingly utilized for scanning organs and provides a reliable method for diagnosing purposes.

The object to be imaged, i.e. in the illustrated example the breast, is placed in a suitably sized and shaped container 11 comprising a liquid. The liquid may for example be water, oil or spirits. The container 11 is arranged in the opening 4 of the patient positioning table 2.

The ultrasonography device 10 comprises a probe, also called scan head, containing one or more acoustic transducers for sending pulses of sound into the object that is being examined. The transducers are capable of generating and detecting ultrasound waves, and are constructed so that ultrasound beams are generated, followed by a pause during which the return waves are detected. This cycle continues during the entire diagnostic procedure. In an embodiment of the invention an array of acoustic transducers are utilized for constructing an image. An ultrasound beam is scanned or swept over the object and a two dimensional image is thereby obtained in a conventional manner. That is, transmitting a sound wave, determining which transducer elements receives the echo or reflection, the strength of the reflection and the time elapsed for the reflection to be received from when the sound was transmitted. The received signals are transformed into a digital image in a way that is known per se to a person skilled in the art. The ultrasonography device 10 thus comprises means for performing these calculations, such as signal processing electronics, which can be of a conventional type. Since the ultrasonography device 10 rotates along with the X-ray source 5 and the X-ray detector 6, three dimensional ultrasonography images are provided.

The ultrasonography device 10 is arranged at a suitable angle from the X-ray detector 6, for example 90°, and transmits and receives a sound wave, as described above. The ultrasonography device 10 is arranged to be moved along the wall of the container as the imaging arrangement rotates around the breast.

The X-ray images and ultrasonography images are taken simultaneously or consecutively when the breast is in the same position in both types of images. The X-ray images and ultrasonography images each provide a 3D image of the breast. Since the images are taken when the breast is at the same position they may be superimposed or compared to each other easily in any suitable way.

By means of utilizing two different imaging means, a very reliable system is provided. In a medical application the system 1 in accordance with the invention provides means by which a very reliable diagnosis can be made.

In FIG. 7 the preferred rotation axis is illustrated at 12, but another rotation axis may be used. The line detectors 6a, 6b, ..., 6n of the detector 6 are preferably arranged in a plane orthogonal to the axis of rotation 12 of the support device 8. At reference numeral 13 the object, i.e. the breast, is indicated.

However, the line detectors 6a, 6b, ..., 6n may alternatively be arranged in parallel with the axis of rotation. That is, the line detectors 6a, 6b, ..., 6n and the collimator 7 may be turned 90° so that the planar X-ray beam 9 and the electrodes 16 and 17 are vertical instead of horizontal.

When the X-ray beams are horizontal, then the object is moved in a vertical direction in relation to the imaging arrangement. Conversely, when the X-ray beams are vertical, then the object is moved in a horizontal direction in relation to the imaging arrangement. In either case, the electrodes 16 and 17 of the line detectors 6a, 6b, ..., 6n are parallel with the incoming X-rays.

It is thus to be noted that the support device 8 can be moved in a horizontal or vertical direction in relation to the object (for example a patient), while being rotated. Alternatively, the support device 8 is only arranged to rotate, while the object is moved in a vertical or horizontal direction in relation to the support device 8.

Although the present invention has been described in connection with a certain medical application, namely mammography, other medical applications are conceivable, for example for scanning the whole body of a patient. It is realized that the invention is valuable and appropriate in other applications as well, besides medical applications. The present invention may be utilized in industrial applications, for example in order to ensure that products manufactured fulfill different quality requirements. Another example of a technical field which may benefit from the present invention is security applications, such as scanning luggage at airports or the like.

When utilized in a medical application, the invention provides lessened discomfort for a patient, since a body part of the patient, for example a breast, can be imaged without requiring compression of the body part. Further, if the two different kinds of examinations are performed, the examinations can be performed almost simultaneously, without he patient having to be moved. This has also the advantage that the images can easily be compared to one another, or even superimposed on top of one another where each examination provides different information to be compared to one another.

In summary, by mean of the innovative imaging system new areas of application of CT-scanning are enabled. In particular, cone beam computed tomography is utilised in a mammography application. The present invention thus provides improvements of the examining of objects by means of cone beam computed tomography, wherein the time required for an examination is minimized. Further, the reliability of the results of an examination method is increased, while still minimizing the duration of the examination. In medical applications, the discomfort for a patient undergoing the examination is minimized, for example in that no compression of the breasts of a patient is needed.

The invention claimed is:

1. An imaging arrangement for imaging an object, wherein said imaging arrangement comprises:
   an X-ray source,
   an X-ray detector arranged to receive X-rays transmitted through said object from said X-ray source, said X-ray detector comprising a stack of direction sensitive line detectors, said line detectors being gaseous-based edge-on line detectors provided with an electron avalanche amplifier, wherein each of said line detectors is adapted to record a number of line images of radiation as transmitted through said object, and a support device to which said X-ray source and said X-ray detector are attached so as to be arranged on opposite sides of said object, wherein said support device is arranged to rotate around said object and wherein said support device and said object are arranged to be linearly movable in relation to each other.

2. The imaging arrangement as claimed in claim 1, further comprising a collimator arranged between said X-ray source and said X-ray detector.

3. The imaging arrangement as claimed in claim 1, wherein said line detectors are arranged in a plane orthogonal to an axis of rotation of said support device.

4. The imaging arrangement as claimed in claim 1, wherein said support device is arranged to be movable along a linear extension of said object.

5. The imaging arrangement as claimed in claim 1, wherein said object is arranged to be movable along an axis parallel to an axis of rotation of said support device.

6. The imaging arrangement as claimed in claim 1, wherein said object is arranged to be movable along an axis perpendicular to an axis of rotation of said support device.

7. The imaging arrangement as claimed in claim 1, further comprising an ultrasonography device attached to said support device.

8. The imaging arrangement as claimed in claim 1, wherein said X-ray detector comprises a stack of line detectors, each being directed towards the X-ray source to allow a ray bundle of said radiation that propagates in a respective one of a plurality of different angles to enter the line detector.

9. The imaging arrangement as claimed in claim 1, wherein in said line detector, electrons are freed as a result of ionization by a respective ray bundle and accelerated in a direction essentially perpendicular to the direction of that ray bundle.

10. The imaging arrangement as claimed in claim 1, further comprising computing means for generating a three-dimensional image of the internals of said object from a large series of one-dimensional X-ray images taken around a single axis of rotation.

11. The imaging arrangement as claimed in claim 10, wherein said computing means is arranged to provide a two-dimensional image of the internals of said object when said support device is rotated around said object one revolution and a three-dimensional image of the internals of said object when said support device is moved along a linear extension of said object.

12. The imaging arrangement as claimed in claim 1, further comprising an additional X-ray source and an additional X-ray detector arranged on said support device.

13. The imaging arrangement as claimed in claim 1, further comprising a filter device capable of operating in two or more operation modes having different filter characteristics.

14. A system for imaging an object, wherein said system comprises an imaging arrangement as claimed in claim 1, wherein said system further comprises a patient positioning table.

15. The system for imaging an object as claimed in claim 14, wherein said patient positioning table comprises an opening in which the object to be imaged is positioned.

16. The system for imaging an object as claimed in claim 15, wherein said imaging arrangement is arranged underneath said patient positioning table and arranged so as to image said object when placed in said opening.

17. The system for imaging an object as claimed in claim 15, wherein a container is provided in said opening, in which container a ultrasonography device is arranged to be moved vertically along a wall of said container as said imaging arrangement rotates around said object.

18. The system for imaging an object as claimed in claim 17, wherein said container comprises a liquid.

* * * * *